United States Patent [19]
Ottow et al.

[11] Patent Number: 5,232,915
[45] Date of Patent: Aug. 3, 1993

[54] 9α-HYDROXY-19,11β-BRIDGED STEROIDS, THEIR PRODUCTION AND PHARMACEUTICAL PREPARATIONS CONTAINING THESE STEROIDS

[75] Inventors: Eckhard Ottow; Gunter Neef; Rudolf Wiechert; Walter Elger; Sybille Beier; Karl-Heinrich Fritzemeier, all of Berlin, Fed. Rep. of Germany

[73] Assignee: Schering Aktiengesellschaft, Berlin and Bergkamen, Fed. Rep. of Germany

[21] Appl. No.: 793,447
[22] PCT Filed: May 23, 1990
[86] PCT No.: PCT/DE90/00383
    § 371 Date: Jan. 14, 1992
    § 102(e) Date: Jan. 14, 1992
[87] PCT Pub. No.: WO90/14354
    PCT Pub. Date: Nov. 29, 1990

[30] Foreign Application Priority Data
May 24, 1989 [DE] Fed. Rep. of Germany ....... 3917274

[51] Int. Cl.$^5$ ................. C07J 63/00; C07J 71/00; C07J 75/00; C07J 53/00; A61K 31/695; A61K 31/66; A61K 31/58; A61K 31/565

[52] U.S. Cl. .................... 514/63; 514/114; 514/169; 514/172; 514/173; 514/176; 514/179; 514/185; 514/229.5; 514/248; 514/250; 514/257; 514/279; 514/379; 514/406; 514/410; 514/493; 514/506; 514/647; 514/681; 540/3; 540/4; 540/47; 540/52; 540/57; 552/505; 552/506; 552/504; 552/510; 544/99; 544/140; 544/154; 544/333; 544/335; 544/369; 544/370; 546/36; 546/38; 546/295; 546/198; 548/148; 548/242; 548/301.7; 548/528; 556/95; 556/436; 558/83; 558/29; 558/32; 558/167; 558/170; 558/423; 558/431; 564/308; 568/27; 568/326; 568/309; 568/423; 568/431

[58] Field of Search ........ 540/3, 4, 47, 52, 57; 556/95, 436; 544/99, 140, 154, 245, 369, 370, 338; 552/504, 505, 506, 510; 548/148, 242, 369, 528, 301.7; 564/308; 568/27, 326, 309, 423, 431; 546/36, 38, 195, 198; 514/185, 229.5, 248, 250, 257, 279, 379, 406, 410, 63, 114, 169, 172, 173, 179, 493, 506, 647, 681

[56] References Cited

U.S. PATENT DOCUMENTS
4,196,203 4/1980 Kapp et al. ............... 552/507
4,447,424 5/1984 Teutsch et al. ............ 552/505
4,544,555 10/1985 Gastaud et al. ............ 552/597

FOREIGN PATENT DOCUMENTS
283428 9/1988 European Pat. Off. ......... 552/510
3717169 12/1988 Fed. Rep. of Germany ..... 552/510

OTHER PUBLICATIONS
Stork, et al., J. ACS, 1982, 104 2321-2323.
Grant and Hackh's Chemical Dictionary (McGraw-Hill Books, New York, 1987) p. 14.
Hutchinson, et al., Tetrahedron Letters 28113 pp. 1313-1316, 1987.
Morrison and Boyd, Organic Chemistry (Bostom, Allyn and Bacon 1979) pp. 622, and 631.

Primary Examiner—Robert T. Bond
Assistant Examiner—E. C. Ward
Attorney, Agent, or Firm—Millen, White, Zelano & Branigan

[57] ABSTRACT

9α-Hydroxy-19,11β-bridged steroids of general formula I

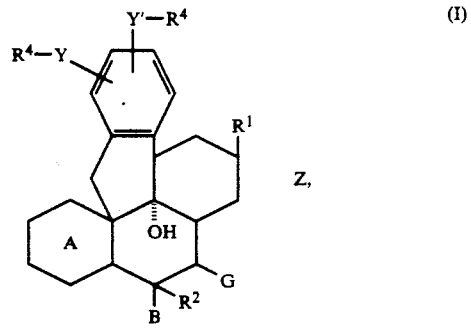

are described. The more detailed meaning of A, B, $R^1$, $R^2$, G, Z, $R^4$—Y and $R^{4'}$—Y' follows from the description. The steroids of general formula I have antigestagen and/or antiglucocorticoidal action and can be used for the production of pharmaceutical agents.

10 Claims, No Drawings

9α-HYDROXY-19,11β-BRIDGED STEROIDS, THEIR PRODUCTION AND PHARMACEUTICAL PREPARATIONS CONTAINING THESE STEROIDS

This invention relates to the object characterized in the claims, i.e., new 9α-hydroxy-19,11β-bridged steroids, process for their production, pharmaceutical preparations containing these compounds, their use for production of pharmaceutical agents as well as the new intermediate products required for this purpose.

The 9α-hydroxy-19,11β-bridged steroids according to the invention are described by general formula I

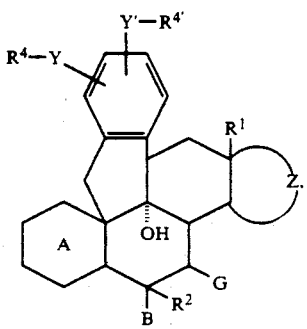

in which
R$^1$ stands for a methyl or ethyl radical,
R$^2$ stands for a hydrogen atom, chlorine atom, a C$_1$-C$_4$ alkyl radical,
B and G, which are the same or different, each stands for a hydrogen atom, a C$_1$-C$_4$ alkyl radical or together for a second bond between carbon atoms 6 and 7,
B and R$^2$ together stand for a methylene or ethylene group,
Z stand for the radical of a ring of formula

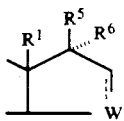

in which
R$^1$ has the meaning mentioned in formula I,
the dotted line starting from W means the possible presence of a double bond,
W means a CH$_2$, CH, CH$_2$CH$_2$ or CHCH$_2$ radical,
R$^5$/R$^6$ means —OR$^7$/—C≡C—U

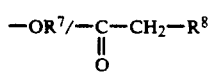

—OR$^7$/—C—CH$_2$—R$^8$
            ‖
            O

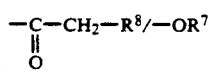

—C—CH$_2$—R$^8$/—OR$^7$
‖
O

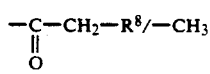

—C—CH$_2$—R$^8$/—CH$_3$
‖
O

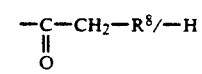

—C—CH$_2$—R$^8$/—H
‖
O

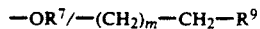

—OR$^7$/—(CH$_2$)$_m$—CH$_2$—R$^9$

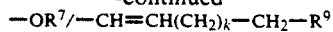

—OR$^7$/—CH=CH(CH$_2$)$_k$—CH$_2$—R$^9$

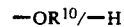

—OR$^{10}$/—H

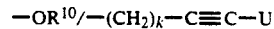

—OR$^{10}$/—(CH$_2$)$_k$—C≡C—U

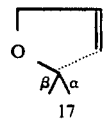

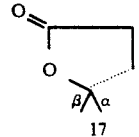

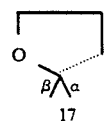

with
R$^7$ meaning a hydrogen atom or acyl radical with 1 to 4 carbon atoms, U meaning a hydrogen atom, an alkyl, hydroxyalkyl, alkoxyalkyl, acyloxyalkyl group each with 1 to 4 carbon atoms in the alkyl or acyl radical or a halogen atom,
R$^8$ meaning a hydrogen atom, a hydroxy group, an alkyl, o-alkyl or o-acyl group each with 1 to 4 carbon atoms,
R$^9$ meaning a hydrogen atom, a hydroxy or cyanide radical, an o-alkyl or o-acyl group each with 1 to 4 carbon atoms,
R$^{10}$ meaning a hydrogen atom, an alkyl or acyl group each with 1 to 10 carbon atoms,
m meaning 0, 1, 2 or 3,
k meaning 0, 1 or 2, in which
R$^4$ and R$^{4'}$, which are the same or different, each stands for a hydrogen atom, a cyanide radical, an —OR$^{11}$, —S(O)$_k$R$^{11}$, —N(O)$_n$R$^{11}$R$^{12}$, —O—SO$_2$R$^{13}$, —P(O)(OR$^{14}$)$_2$, —SiR$^{14}$$_3$ or —SnR$^{14}$$_3$ group with k meaning numbers 0, 1 or 2, n meaning numbers 0 or 1,
R$^{11}$ meaning a hydrogen atom or a C$_1$-C$_8$ alkyl radical,
R$^{12}$ meaning R$^{11}$, a cyanide or a C$_1$-C$_{10}$ acyl radical,
R$^{13}$ meaning a perfluorinated C$_1$-C$_4$ alkyl radical,
R$^{14}$ meaning a C$_1$-C$_4$ alkyl radical or
R$^{11}$ and R$^{12}$ form a 5- or 6-membered heterocyclic ring inside an —N(O)$_n$R$^{11}$R$^{12}$group together with the inclusion of N, and still another heteroatom N, O or S can be contained in the ring,
Y and Y', which are the same or different, each means a direct bond, a straight-chain or branched alkylene group with up to 20 carbon atoms optionally exhibiting a double or triple bond or bonds, the alkylene group is optionally substituted by one or more oxo, C$_1$-C$_{10}$ acyloxy, —OR$^{11}$, —S(O)$_k$R$^{11}$ and/or —N(O)$_n$R$^{11}$R$^{12}$- group or groups, an optionally substituted arylene radical or
R$^4$—Y and R$^{4'}$—Y' together mean the radical of a saturated, unsaturated or aromatic 5- or 6-membered ring optionally substituted with 0 to 2 oxygen atoms, sulfur atoms and/or NR$^{11}$ groups, provided that only then are k and n greater than 0, if $R^{11}$ stands for a $C_1$–$C_8$ alkyl radical and ring A stands for

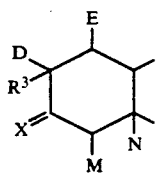   a)

and M and N together mean a second bond or M means a hydrogen atom and N means a hydroxy group, and then B, $R^2$, G, $R^3$, D and E are hydrogen atoms, and X means an oxygen atom, two hydrogen atoms or a hydroxyimino grouping N~OH, $R^3$ and D, which are the same or different, each means a hydrogen atom, a nitrile radical or a $C_1$–$C_4$ alkyl radical or together a methylene or ethylene group, E means a hydrogen atom, a $C_1$–$C_4$ alkyl radical, D and E together mean a second bond between carbon atoms 1 and 2 or together mean a methylene group or

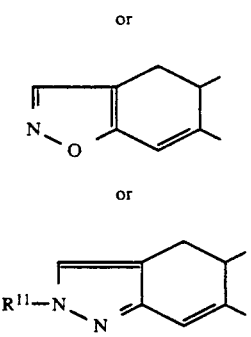   b)

or c)

with $R^{11}$ meaning a hydrogen atom or a $C_1$–$C_8$ alkyl radical, as well as optionally their pharmaceutically compatible addition salts with acids.

If Y—$R^4$=H and Y' is the ethylene group substituted in 1-positions with an oxo group and $R^{4'}$=H, the acetyl group is present as Y'—$R^{4'}$, which has a preferred role within the scope of the invention.

In the substitution of the phenyl ring, the monosubstitution in 3-, 4- or 5-position as well as the disubstitution in 4- and 5- or 3- and 4- position with the formation of a fused second ring, for example, a cyclohexene, pyrrole, furyl, pyrroline, 1,3dioxacyclopentene, pyrazoline, didehydromorpholine, didehydropiperidine, didehydropiperazine, dihydropyran, pyrimidine, pyridine, pyrazine, 1,4-dioxacyclohexene ring, is preferred.

The alkyl radicals standing for $R^1$ and $R^{11}$ or $R^2$, $R^3$, B, G and D are to have 1 or 2 carbon atoms in the case of $R^1$, 1 to 8 and otherwise 1 to 4 carbon atoms in the case of $R^{11}$, and the methyl, ethyl, propyl, isopropyl, butyl or methyl, ethyl, propyl groups are preferred.

If $R^{12}$ stands for an acyl radical, the formyl, acetyl, propionyl, butyryl and benzoyl group is preferred.

$R^{11}$ and $R^{12}$ together with the inclusion of he nitrogen atom also stand for a heterocyclic, 5- or 6-membered ring, which apart from N and C atoms, can also contain in addition an O or S atom; for example, there can be mentioned the pyrrole, pyrrolidine, piperidine, piperazine, morpholine, oxa and thiazolidine as well as thiadiazolidine ring.

The alkyl, alkoxy as well as acyloxy groups contained in $R^5$ and $R^6$ or $R^7$, $R^8$, $R^9$, $R^{10}$ and U of general formula I each are to contain 1 to 4 carbon atoms, and the methyl, ethyl, propyl, isopropyl, methoxy, ethoxy, propoxy, isopropoxy, formyl, acetyl, propionyl and isopropionyl groups are preferred.

Of the alkenyl radicals in $R^6$, the propenyl and butenyl groups, which can be present in the E- or Z-configuration, are preferred, i.e., if $R^6$ stands for —CH═CH—$(CH_2)_k CH_2$—$R^9$, then k is to mean preferably 0 or 1.

The new compounds of general formula I are produced according to the process of the invention according to claim 1.

The production of the intermediate products of general formula II

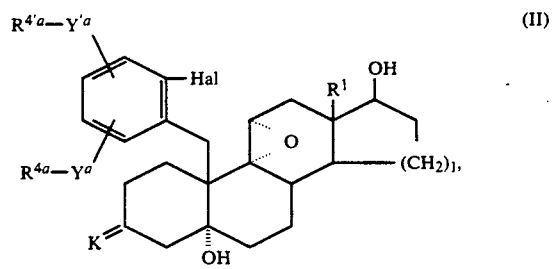   (II)

in which $R^1$ means a methyl or ethyl radical, 1 means numbers 1 or 2,

K means a keto group blocked in the form of ketal or thioketal, and

Hal means a chlorine, bromine or iodine atom, $R^{4a}$, $R^{4'a}$, Ya and $Y'^a$, with exclusion of the cyanide radical, have the same meaning as $R^4$, $R^{4'}$, Y and Y', and optionally present hydroxy, mercapto, amino, oxo and-/or terminal acetylene groups are protected, which are also an object of the invention, is based on the compounds of formula IIIa described in European patent application EP-A 0281 428

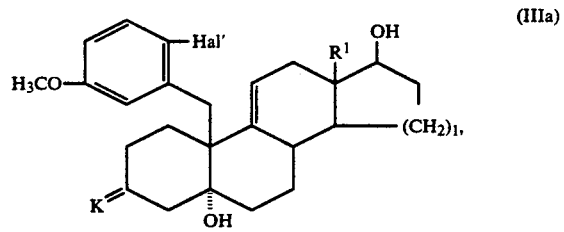   (IIIa)

in which $R^1$ and K, which have the above-mentioned meaning,

Hal' stands for a chlorine or bromine atom or on the compounds of general formula IIIb obtainable according to the instructions likewise contained in EP-A 0283428

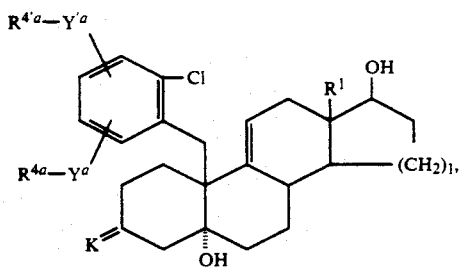

(IIIb)

in which $R^{4'a}$, $Y'^a$, $R^{4a}$ and $Y^a$ as well ad K, 1 and $R^1$ have the meanings already mentioned above.

In the compounds of general formulas IIIa or IIIb, the chlorine atom in 2-position of the phenyl ring is generally to be exchanged for a bromine (or iodine) atom before the further reaction, for example, under the conditions mentioned in example 8a), b).

In the next step, a compound of general formula IIIa or IIIb is then converted to a compound of general formula II by epoxidation of the 9,11-double bond, for example, by reaction with a peracid, for example according to the instructions described in J. Org. Chem., 38, no. 12, p. 2267 (1973) or J. Org. Chem., 44, no. 8, p. 1351 (1979 . Preferably m-chloroperbenzoic acid is used as epoxidation agent.

Under protection of the functional groups optionally present in the 19-phenyl ring, the new compounds of general formula II are subjected to a cyclization.

The hydroxy, mercapto and keto protecting groups encompassed by K are groups which are easily cleavable in acid medium, such as, for example, the methoxymethyl, ethoxymethyl, tetrahydropyranyl, ethylenedioxyketal, ethylenedithioketal or 2,2-dimethyltrimethylenedioxyketal group. One (or more) hydroxy group or groups present on the 19-phenyl ring is or are protected by a group to be removed in a basic manner, for example, by a methoxy group. The latter can be cleaved off again, for example, by reaction with sodium thiophenolate. Protecting groups for amino groups and terminal acetylene groups (for example, the trimethylsilyl and tert-butyldimethylsilyl group) are also known to one skilled in the art and are cleaved according to the desired reaction sequence also according to processes known in the literature [Synthesis 1980, 627, J. Org. Chem. 46 (1986) 2280].

The conversion of II to the new 9o-hydroxy-19,11β-bridged steroids of general formula IVb

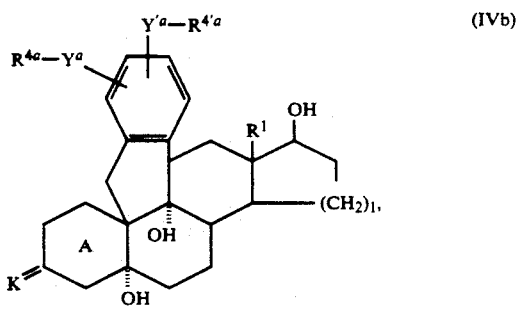

(IVb)

in which $R^1$, K and 1 as well as $R^{4'a}$, $Y'^a$, $R^{4a}$ and $Y^a$ have the above-mentioned meaning and are also the object of the invention, takes place with an aryl anion as a reactive species, which can be formed after a halogen-metal exchange of the orthochlorine, bromine (or iodine) atom in the 19-phenyl ring of the compound of general formula II for an $Me^{(+)}$, $MgX^{(+)}$, $Cu^{(+)}$ or $CuX^{(+)}$ ion ($Me^{(+)}$ =alkali ion, X=Cl, Br, I).

For example, n-butyllithium (cf. example 1b), t-butyllithium or metallic lithium is used in an inert solvent such as diethyl ether to bring about the halogen-metal exchange and, after that, the cyclization to a compound of general formula IVb.

It had to be a surprise that in this case, a 6-membered ring (ring closure to the 11 C atom) and not a 5-membered ring (ring closure to the 9 C atom) is formed. In a similar case, only the formation of a 5-membered ring had been observed (cf. J. Org. Chem., 43. no. 19, p. 3800 (1978) and the Baldwin Rules in J. Chem. Soc., Chem. Commun. 734 (1976)).

The conversion of the thus obtained cyclization products in the finally desired end products of general formula I takes place analogously to the process known in the literature (for example, J. Fried, J. A. Edwards, "Organic Reactions in Steroid Chemistry," Van Nostrand Reinhold Company 1972, Vol. 1 and 2; "Terpenoids and Steroids," Specialist Periodical Report, The Chemical Society, London, Vol. 1-12)

by either first a) the C-17 hydroxy group being oxidized and then b) optionally a hydroxy group, exhibiting a protecting group, being liberated from this protecting group in the 19,11β-phenylene ring, a corresponding perfluoroalkylsulfonate ($C_1$–$C_4$) optionally being produced from the hydroxy compound, the perfluoroalkylsulfonate being converted to a compound optionally either directly or by exchange of the perfluoroalkylsulfonate leaving group for a tin trialkyl group by the corresponding tin trialkyl compound, which exhibits the desired substitution pattern in the 19,11β-phenylene ring, optionally after further reactions, or first b) and then a) being performed and then c) ring D being functionalized in a desired way according to methods known in the art, the thus obtained product from the action of a dehydrating agent, which is also capable of releasing the 3-oxo group, being subjected to dehydration with the simultaneous formation of the 4(5)-double bond, and optionally the release of the 3-oxo group and the dehydration taking place in succession, and then, optionally after renewed protection of intermediately released functional groups contained in the 19,11β-phenylene ring and/or Z, the desired functions of rings A and B of the steroid skeleton being introduced or d) the thus obtained product of the action of a dehydrating agent, which is also capable of releasing the 3-oxo group, being subjected to the dehydration with the simultaneous formation of the 4(5)-double bond, the desired functions of rings A and B of the steroid skeleton being introduced and then, after protection of the 3-oxo group, ring D being functionalized in the desired way, or steps a) and b) being performed after step c) or d), the thus obtained product optionally being liberated from the protecting groups, the hydroxy, mercapto and/or amino group or groups optionally contained in the 19,11β-phenylene ring optionally being alkylated or acylated, a cyanide radical optionally being introduced in the aryl substituent or substituents, the amino and/or sulfide group or groups optionally contained in the aryl substituent or substituents optionally being oxidized, optionally being reacted with hydroxylaminehydrochloride to the product of general formula I with X meaning hydroxyimino grouping N~OH as well as a pharmaceutically compatible acid addition salt optionally being produced.

In the course of these reaction paths, it can become necessary to introduce intermediately again protecting groups in intermediate products, for example, for functional groups, contained in Z, in subsequent functionalization of rings A and B or for the 3-keto group in subsequent build-up of ring D.

The oxidation of the 17β-hydroxy group necessary for the production of almost all end products is performed in a way known in the art, for example, by Oppenauer oxidation or with chromic acid reagents (Jones' reagent or chromic acid pyridine).

The release of the 3-keto function with simultaneous dehydration and formation of the 4(5)-double bond takes place by treatment with acid or an acid ion exchanger. The acid treatment takes place in a way known in the art, by the corresponding 5α-hydroxy-3-ketal being dissolved in a water-miscible solvent, such as, aqueous methanol, ethanol or acetone, and catalytic amounts of mineral acid or sulfonic acid, such as, hydrochloric acid, sulfuric acid, phosphoric acid, perchloric acid or p-toluenesulfonic acid, or an organic acid, such as acetic acid, being allowed to act on the solution until existing protecting groups are removed and water optionally is separated. The reaction, which occurs at temperatures of 0° to 100° C., can also be performed with an acid ion exchanger. The course of the reaction can be followed with analytical methods, for example, by thin-layer chromatography of gathered samples.

In general, the removal of the protecting groups and dehydration is achieved in one reaction step by the corresponding 5α-hydroxy-3-ketal or 5-ene-3-ketal being allowed to react in a strongly acidic medium for a certain period, as is described in example 1i). But just as it is possible according to the invention to perform the removal of the protecting groups and dehydration in two reaction steps separated from one another, first by the corresponding 5α-hydroxy-3-keto compound being obtained first by a shorter treatment of the corresponding 5α-hydroxy-3-ketal in moderately acidic medium and optionally at a temperature of 0° C. or below and optionally being isolated, as is shown by way of example in example 8. The 5α-hydroxy-3-keto compound is then converted to the 3-keto-4-ene compound by further allowing acid to act under dehydration.

The selective removal of the protecting group without dehydration is possible in some cases also in strongly acidic medium (e.g., 4 n HCl), if it is allowed to react only for a short time at 0° C. or below.

A quite special advantage of this invention lies in the large bandwidth of the substituents introducible at the 19-phenyl radical (M. Pereyre, J.-P. Quintard, A. Rahm, Tin in Organic Synthesis: Butterworths, 1987). For one thing, substituents $R^4$—Y— or $R^{4'}$—Y'— present in the later end product can be introduced directly by a compound of general formula IIIb (cf. EP-A 0283 428).

With another embodiment of the process according to the invention, it is possible to vary the substituent or substituents in the 19,11β-phenylene radical over a wide range, by the substituent or substituents first being introduced after the cyclization, namely before, simultaneously with or only after the finishing of the structure of rings A, B and D. For this purpose, at least one of the hydroxy groups present and protected in the 19,11β-phenylene radical in formula IVb is liberated from its protecting group and the corresponding perfluoroalkylsulfonate compound is produced from the free OH compound by reaction with perfluoroalkylsulfonic acid anhydride (alkyl=$C_1$-$C_4$) according to methods known in the art (P. J. Stang, M. Hanack and L. R. Subramanian, *Synthesis* 85 (1982)].

In this case, either the perfluorosulfonate leaving group is displaced with basically almost simultaneous substitution by the desired substituent or its precursor in a reaction catalyzed by transition metal (preferably Pd⁰) (J. E. McMurry and S. Mohanraj, Tetrahedron Letters, 24, no. 27, pp. 2723-2726, 1983; X. Lu and J. Zhu, Communications, pp. 726-727, 1987; Q.-Y. Chen and Z.-Y. Yang, Tetrahedron Letters 27, no. 10, pp. 1171-1174, 1986; S. Cacchi, P. G. Ciattini, E. Morera and G. Ortar, Tetrahedron Letters, 27, no. 33, pp. 3931-3934, 1986; A. M. Echavarren and J. K. Stille, J. Am. Chem. Soc. 1987, 109, pp. 5478-5486) or a corresponding triorganylstannyl, preferably a tri-n-alkylstannyl compound, intermediately and catalyzed by transition metal, is produced from the perfluoroalkylsulfonate compound [J. K. Stille, Angew. Chem. [Applied Chem.] 98 (1986), pp. 504-519]. The latter is then reacted with a halogen-, preferably bromine- or iodine-substituted carbocyclic (cf. example 6c) or heterocyclic aromatic substance (cf. example 3b) [Y. Yamamoto, Y. Azuma, H. Mitoh, Communications, pp. 564-565, 1986; T. J. Bailey, Tetrahedron Letters, 27. no. 37, pp. 4407-4410, 1986], which optionally can have even further substituents; the 19,11β-phenylene radical then exhibits in it the desired substitution or a precursor of the desired substitution. The precursors are further processed to the finally desired compounds according to standard methods of organic chemistry.

If the 19-phenyl ring exhibits two protected hydroxy groups, to start with only the protecting group of one (the first) hydroxy group can be selectively removed, the free hydroxy group can be functionalized, then optionally the protecting group of the second hydroxy group can be cleaved off and this hydroxy group can be modified, optionally also by reaction with the function now found on the first hydroxy group.

The introduction of 1,2 and/or 6,7-double bonds besides the 3,4-double bond is possible according to known methods, for example, with dehydrating agents, such as seleniumdioxide, chloranil, thallium triacetate or dichlorodicyanobenzoquinone (DDQ).or by allyl or dienol ether bromation and subsequent hydrobromic acid cleavage [J. Fried, J. A. Edwards, Organic Reactions in Steroid Chemistry, Van Nostrand Reinhold Company 1972, pp. 265-374, 1; Tetrahedron 42, (1986) 2971].

The allyl bromation is performed in a solvent, for example, with N-bromosuccinimide, N-bromoacetamide, 1,3-dibromo-5,5-dimethylhydantoin or dibromotetrachloroethane in the presence of a radical former such as dibenzoyl peroxide. As solvent, aprotic solvents such as dioxane and chlorinated hydrocarbons, such as, for example, carbon tetrachloride, chloroform or tetrachloroethylene are suitable. The reaction takes place between 0° C. and the boiling temperature of the solution.

The dienol ether bromation is performed, for example, analogously to the instructions in Steroids I, 233.

The hydrobromic acid cleavage with formation of the $\Delta^6$-double bond takes place by heating the 6-bromine compound with basic agents, preferably with lithium bromide and lithium carbonate or with lithium bromide and calcium carbonate in an aprotic solvent, such as dimethylformamide, at temperatures of 50° to 120° C. Another possibility of the HBr cleavage consists in that the 6-bromine compound is heated in collidine or lutidine.

Starting from a saturated ring A, double bonds can be introduced simultaneously in 1,2- and 4,5-position, for example, by bromation to 2,4-dibromo-3-ketone and dehydrobromation of the dibromide with, for example, lithium or calcium carbonate and lithium bromide in dimethylformamide.

The introduction of a 6-methylene group can take place, for example, starting from a 3-amino-3(4),5(6)-diene derivative by reaction with formalin in alcoholic solution (Helv. Chim. Acta. 56 (1973) 2396) to the 6α-hydroxymethyl group and then acidic dehydration, for example, with hydrochloric acid in dioxane/water or starting from a 3-alkoxy-3(4),5(6)-diene derivative, analogously to the method described in U.S. Pat. No. 4,544,555 or directly, starting from a 3-oxo-4(5)-ene derivative analogously to the instructions in Synthesis (1982) 34.

The methylenation of the 6-methylene compound to the 6,6-ethylene compound takes place with dimethylsulfoxonium methylide. For this purpose, the 6-methylene steroid is added to a suspension of trimethylsulfoxonium iodide with sodium hydride in mineral oil and dimethylsulfoxide or to a solution of trimethylsulfoxonium iodide and sodium hydroxide in dimethyl sulfoxide. The reaction is completed after 15 to 60 minutes at 20° to 40° C. (J. Am. Chem. Soc. 84 (1962) 866; European patent application 0150157). The introduction of a 2-methylene group takes place analogously to the method of A. J. Manson and D. Wood [J. Org. Chem. 32 (1967) 3434] or the methods cited there.

The methylenation of the 2-methylene compound to the 2,2-ethylene compound takes place analogously to the methylenation of the 6-methylene compound [also see Chem. Ber. 98 (1965) 1470].

Monoalkylated or dialkylated compounds in 2-position can be obtained, for example, analogously to the method of L. Nedelec, Tetrahedron 30 (1974) 3263.

Alkylated compounds in 1- or 7-position are obtained by 1,4- or 1,6-addition to the corresponding enones according to known methods (J. Fried, J. A. Edwards: Organic Reactions in Steroid Chemistry, Van Nostrand Reinhold Company 1972, pages 75 to 82, 2; and J. Am. Chem. Soc. 99 1977) 1673).

Alkylated compounds in 6-position can be obtained, for example, by opening the corresponding 5α,6α-epoxides and secondary reactions (J. Fried, J. A. Edwards: Organic Reactions in Steroid Chemistry, Van Nostrand Reinhold Company 1972, pages 82-86, 2).

1α-, 2α-, 6α-, 7α-, 6β-, 7β-methylene compounds or a combination of the 1α,2α-methylene structural element with both 6,7-methylene structural elements allow the corresponding allyl alcohols to be obtained by adding diazomethane or dimethylsulfoxonium methylide to the corresponding enones or by a Simmons-Smith reaction (J. Fried, J. A. Edwards: Reactions in Steroid Chemistry, Van Nostrand Reinold Company 1972, pages 100-126; Rev. Soc. Quim. Mex. (1969) 171A; Chem. Ber. 101 (1968) 935; Chem. Ber. 99 (1966) 1118; Zeitschr. f. Naturf., 19b (1964) 944).

The production of the isoxazole ring annelated on 2- and 3- positions takes place by the synthesis of the 2-hydroxymethylene compounds [Steroids 6 (1962) 178; J. Amer. Chem. Soc. 83 (1961) 1478]and their reaction with hydroxylamine [J. Med. Chem. 6 (1963) 1].

[2,3-d]Isoxazoles are also good initial materials for the synthesis of 2-cyano steroids [J. Med. Chem. 6 (1963) 1].

The production of the pyrazole ring annelated in 2- and 3-positions takes place by reaction of 2-hydroxymethylene-3-oxo feedstocks with $R^{11}$-substituted hydrazine (US patent 3,704,295).

The introduction of chlorine or methyl substituents in C-6 of the steroid skeleton is possible, e.g., by the methods indicated in German laid-open specification 1,158,966 or in U.S. Pat. No. 4,544,555 and U.S. Pat. No. 4,196,203 by the corresponding 6,7-epoxides or 6-methylene derivatives as well as by oxidation of the 6-chloro-3,5-dienol ether with dichlorodicyanobenzoquinone (DDQ) under acidic conditions [Belgian patent 621,197 (1962)].

The removal of the 3-oxo group for an end product of general formula I with X meaning two hydrogen atoms can take place, e.g., according to the instructions indicated in DOS 2805490 by thioketalization and subsequent reductive cleavage.

Feedstocks with a D-homo-steroid skeleton are also to be obtained, e.g., by Tiffeneau rearrangement analogously to the instructions published in Australian J. Chem. 8 (1955), 519 and in "Organic Reactions in Steroid Chemistry" Vol. 2, 388. The necessary 17α-aminomethyl-17β-hydroxy compounds are accessible, for example, by the opening of the 17,20-spiroepoxides with ammonia or also by lithium aluminum reduction of the acetylated 17β-hydroxy-17α-cyano compounds. The spiroepoxides are accessible by conversion of the corresponding 17-ketones with dimethylsulfonium methylide to dimethylformamide [Journal f. prakt. Chemie 314 (1972), 667-668). The acetylated cyanohydrines are accessible by adding cyanohydrogen to the corresponding 17-ketones and subsequent acetylation according to known instuctions (e.g., Australian J. Chem. 8 (1955), 519).

Feedstocks with an unsaturated D-ring are accessible, for example, by modified Saegusa oxidation (Tetrahedron 42 (1986) 2971) of the corresponding enol compounds of the 17-ketone. For example, the trimethylsilylenol ether can be produced by converting the 17-ketone with lithium diisopropylamide in tetrahydrofuran to the corresponding enolate and trapping by trimethylchlorosilane (Synthesis 1983. 1).

The introduction of substituents $R^5$ and $R^6$ takes place according to the usual process of the C-17 side chain synthesis by nucleophilic addition to the 17-ketone—obtained by, e.g., Oppenauer oxidation of the C-17 hydroxy group—and secondary reactions ("Terpenoids and Steroids," Specialist Periodical Report, The Chemical Society, London, Vol. 1-12).

The introduction of substituents —C≡C—U as $R^6$, and U has the above-mentioned meaning, takes place with the help of a compound of general formula MC≡C—U', in which U is an alkine protecting group, such as, for example, the trimethylsilyl or tert-butyldimethylsilyl radical, or else if U is an alkyl group with 1–4 C atoms, U' itself is radical U.

The organometallic compound can also be formed in situ and brought to reaction with the 17-ketone. Thus, acetylene and an alkali metal, in particular potassium, sodium or lithium, can be allowed to act in the presence of an alcohol or in the presence of ammonia for example on the 17-ketone in a suitable solvent. The alkali metal can also take effect in the form of, for example, methyllithium or butyllithium. As solvent, in particular dialkyl ether, tetrahydrofuran, dioxane, benzene and toluene are suitable.

The introduction of 3-hydroxypropine, 3-hydroxypropene or 3-hydroxypropane in 17-position takes place by reacting 17-ketone with the dianion of propargyl alcohol (3-hydroxypropine), for example, the dipotassium salt, generated in situ, of the propargyl alcohol, to the 17α-(3-hydroxyprop-1-inyl)-17β-hydroxy derivative or with metalated derivatives of 3-hydroxypropine, for example, with 1-lithium-3-(tetrahydropyran-2'-yloxy)-prop-1-in-1-ide, to the 17-[3-(tetrahydropyran-2'-yloxy)-prop-1-inyl]-17β-hydroxy derivative, which then can be hydrogenated to the 17-(3-hydroxypropyl- or hydroxypropenyl)17β-hydroxy compounds. This is possible, for example, by hydrogenation at room temperature and standard pressure in solvents such as methanol, ethanol, propanol, tetrahydrofuran (THF) or ethyl acetate by adding noble metal catalysts such as platinum or palladium.

The introduction of homologous hydroxyalkine, hydroxyalkene and hydroxyalkane groups takes place in a corresponding way with homologues of propargyl alcohol.

The compound with the Z-configured double bond in the hydroxypropenyl group results by hydrogenation of the acetylenic triple bond with a deactivated noble metal catalyst (J. Fried, J. A. Edwards: Organic Reactions in Steroid Chemistry, Van Nostrand Reinhold Company 1972, page 134; and H. O. House: Modern Synthetic Reactions 1972, page 19). As deactivated noble metal catalysts, for example, 10% palladium on barium sulfate in the presence of an amine or 5% palladium on calcium carbonate with adding lead(II) acetate is suitable. The hydrogenation is broken off after the absorption of one equivalent of hydrogen.

The compound with the E-configured double bond in the hydroxypropenyl group results by reduction of the acetylenic triple bond in a way known in the art. In the literature, an entire series of methods to convert alkines into trans-olefins is described, for example, the reduction with sodium in liquid ammonia (J. Am. Chem. Soc. 63 (1941) 216), with sodium amide in liquid ammonia (J. Chem. Soc. 1955, 3558), with lithium in low-molecular amines (J. A. Chem. Soc. 77 (1955) 3378), with boranes (J. Am. Chem. Soc. 93 (1971) 3395 and 94 (1972) 6560), with diisobutylaluminum hydride and methyllithium (J. Am. Chem. Soc. 89 (1967) 5085) and in particular with lithiumaluminum hydride/alcoholate (J. Am. Chem. Soc. 89 (1967) 4245). Another possibility is the reduction of the triple bond with chromium(II) sulfate in the presence of water or dimethylformamide in weakly acidic medium (J. Am. Chem. Soc. 86 (1964) 4358) as well as generally the reduction by the action of transition metal compounds with alternation of the oxidation stage.

The introduction of the hydroxyalkenes can also take place directly by adding a corresponding metalated hydroxyalkenyl compound, such as, for example, 1-lithium-3-(tetrahydropyran-2'-yloxy)-prop-1(E)-ene (J. Org. Chem. 40 2265) or 1-lithium-3-(tetrahydropyran-2'-yloxy)-prop-1(2)-ene (Synthesis 1981, 999). Homologues can also be introduced in this way.

The introduction of 3-hydroxypropane in 17-position can also take place directly by reaction of the 17-ketone with metalated derivatives of 3-halopropanols—and the hydroxy group in the metalation step is present as alcoholate (Tetrahedron Letters 1978, 3013) or as a protected function (J. Org. Chem. 37, 1947) —to the 17-(3-hydroxypropyl)-17β-hydroxy compound or to the compound protected on the terminal hydroxy group. As protecting groups, for example, the ethoxyethyl, tetrahydropyranyl and methoxymethyl groups are suitable.

If end products of formula I are desired with $R^5/R^6$ meaning

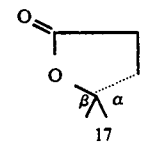

the 17-(3-hydroxypropyl) compound is oxidized in a way known in the art, for example, with Jones' reagent, manganese dioxide, pyridinium dichromate, pyridinium chlorochromate, chromic acid pyridine or the Fetizon reagent silver carbonate/Celite (Compt. rend. 267 [1968] 900).

The production of end products of formula I with $R^5/R^6$ meaning

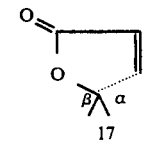

takes place by ring closure reaction of the corresponding 17-(3-hydroxyprop-1-(Z)-enyl-17β-hydroxy feedstock.

If $R^5/R^6$ together stand for

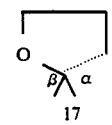

either an above-described dihydrofuran compound is catalytically hydrogenated or the corresponding 17-(3-hydroxypropyl)-17β-hydroxy compound is cyclized.

The synthesis of the 17-cyanomethyl side chain takes place in a way known in the art from the 17-ketone, for example, by the 17-spiroepoxide and cleavage of the spiroepoxide with HCN according to Z. Chem. 18 (1978) 259–260.

Also, the introduction of the 17-hydroxyacetyl side chain takes place according to methods known in the art, for example, according to the methods described in J. Org. Chem. 47 (1982), 2993–2995, Chem. Ber. 113 (1984), 1184 or U.S. Pat. No. 4,600,538.

To introduce the groupings

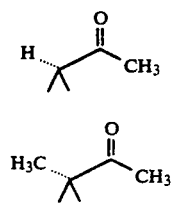

17-ketone is converted with tosylmethyl isocyanide (Chem. Ind. 1972 213) to the 17-nitrile compound (Tetrahedron 31 (1975), 2151), which can be converted directly with methyllithium or methylmagnesium bromide to the 17-acetyl compound, which yields the desired 17α-methyl-17β-acyl grouping after enolization with k-tert0butylate in tetrahydrofuran and reaction with methyl iodide. This sequence of adding methyl to the nitrile and subsequent alkylation can also be performed in reverse sequence.

Free hydroxy or hydroxy, mercapto and/or amino groups present in Z or in the 19,11β-phenylene ring can be alkylated or acylated in a way known in the art.

Sulfides and/or dialkylamines contained in the 19,11β-phenylene ring can be converted by suitable oxidizing agents (for example, hydrogen peroxide or peracids) to the desired sulfoxides (n=1), N-oxides (n=1) [see, e.g., Kontakte [Contacts] (Darmstadt) 1986, 3, p. 12] or sulfones (n=2).

Compounds with a dialkylamine substituent in the 19,11β-phenylene ring can be converted to the corresponding (N-cyano-N-alkylaminoaryl) derivatives by reaction with bromocyanogen in aprotic solvents such as, for example, dioxane, benzene or toluene at elevated temperature (amine degradation according to Braun) analogously to the instructions indicated, for example, in Org. Reactions 7, 198 (1953), K. W. Bentley, Techniques of Organic Chemistry 11, 773 (1963) and Houben-Weyl, 5/4, 151 (1960) in good yields.

The latter are reduced depending on the finally desired meaning of $R^{12}$ in the end product in a way known in the art to the corresponding dialkylamine compounds (for example, with diisobutylaluminum hydride in toluene to the N-formyl-N-alkylaminophenyl intermediate products and then with lithiumaluminum hydride) or N—H—N—alkyl compounds (for example, with lithiumaluminum hydride or with lithium in liquid ammonia). The latter are then optionally acylated in a way known in the literature and optionally then reduced in a known way with, for example, lithiumaluminum hydride to the new dialkylamine derivative (see DE 36 23 038).

The obtained compounds of general formula I with X meaning an oxygen atom can optionally be converted by reaction with hydroxylamine hydrochloride in the presence of tertiary amines at temperatures between −20° and +40° C. in the oximes (formula I with X meaning the hydroxyimino grouping N OH, and the hydroxy group can be in syn-position or anti-position). Suitable tertiary bases are, for example, trimethylamine, triethylamine, pyridine, N,N-dimethylaminopyridine, 1,5-diazabicyclo[4.3.0]nonene-5 (DBN) and 1,5-diazabicyclo[5.4.0]undecene-5 (DBU), and pyridine is preferred. The new compounds of general formula I as well as their addition salts with pharmaceutically compatible acids are valuable pharmaceutical agents. Thus, they have at their disposal a strong affinity to the gestagen receptor and have a surprisingly large range of antigestagen, antiglucocorticoidal and antimineralcorticoidal properties. These important biological activities can be used for medicinal purposes.

Active ingredients of this type with pronounced antigestagen activity are suitable for inducing abortions, since they displace by receptor the progesterone necessary for maintaining the pregnancy. Therefore, they are valuable and advantageous in view of their use for postcoital birth control.

They can also be used for treatment of hormonal irregularities, for inducing menstruation, for inducing labor and for treating endometriosis. Further, they can be used for the treatment of hormone-dependent cancers.

To determine the antigestagen activity of the compounds of general formula I, the rat abortive test described in EP-A 0283 28, page 12, was performed as a typical example with 9α,17β-dihydroxy-17-(prop-1-inyl)-11β,19-[4-(3-pyridyl)-o-phenylene]-4-androsten-3-one:

| Dose s.c. mg/animal/d | n abortions/n treated |
|---|---|
| 3.0 | 4/4 |
| 1.0 | 4/4 |
| 0.3 | 2/4*) |
| controls benzyl benzoate/caster oil (1:4) | 0/4 |

*)pathological nidation points

The compounds of general formula I according to the invention as well as their addition salts with pharmaceutically compatible acids also exhibit an antiglucocorticoidal activity and can thus also be used as pharmaceutical agents for the treatment of corticoid-induced disorders (glaucoma) as well as for control of side effects, which occur with long-term treatment with glucocorticoids (Cushing Syndrome). They therefore make it possible also to control the disorders attributable to a hypersecretion of the glucocorticoids, above all obesity, arteriosclerosis, hypertension, osteoporosis, diabetes as well as insomnia.

The compounds of general formula I according to the invention as well as their addition salts with pharmaceutically compatible acids with antimineralcorticoidal properties can be used to treat disease conditions, in which a hyperaldosteronism is involved.

Thus, the invention relates also to pharmaceutical agents based on pharmaceutically compatible, i.e. nontoxic in the doses used, compounds of general formula I as well as their addition salts with pharmaceutically compatible acids, optionally together with the usual auxiliary agents and vehicles.

The compounds according to the invention and their salts can be processed according to the methods of galenicals known in the art to pharmaceutical preparations for enteral, percutaneous, parenteral or local administration. They can be administered in the form of tablets, coated tablets, gel capsules, granular powders, suppositories, implants, injectable, sterile, aqueous or oily solutions, suspensions or emulsions, ointments, creams and gels.

The active ingredient or ingredients can be mixed in this case with the auxiliary agents usual in galenicals such as, e.g., gum arabic, talc, starch, mannitol, methyl cellulose, lactose, surfactants such as Tweens ® or Myrj ®, magnesium stearate, aqueous or nonaqueous vehicles, paraffin derivatives, wetting agents, dispersing agents, emulsifiers, preservatives and aromatic substances for taste correction (e.g., ethereal oils).

Thus, the invention also relates to pharmaceutical compositions, which as active ingredient contain at least one compound according to the invention or one of their addition salts with pharmaceutically compatible acids.

As addition salts of the products with acids according to the invention, hydrochloride and methanesulfonate can be mentioned in particular.

A dosage unit contains about 1-100 mg of active ingredient or ingredients.

The dosage of the compounds according to the invention in humans is about 1-1000 mg per day.

The following examples explain the production of the compounds according to the invention.

EXAMPLE 1

9α,17β-Dihydroxy-11β,19-(4-ethyl-o-phenylene)-17-(prop-1-inyl)-4-androsten-3-one a)

19-(2-Bromo-5-methoxyphenyl)-3,3-(2,2-dimethyltrimethylenedioxy)-9α,11α-epoxy-androstane-5α,17β-diol 225 ml of a 0.5 m aqueous sodium bicarbonate solution and 22.6 g of 67% m-chloroperbenzoic acid are added in succession to a solution of 47.6 g (82.6 mmol) of 19-(2-bromo-5-methoxyphenyl)-3,3-(2,2-dimethyltrimethylenedioxy)-9,11-androstene-5α,17β-diol in 0.8 l of methylene chloride at room temperature. Then, the reaction mixture is stirred for 1.5 more hours. For working up, the aqueous phase is separated, it is extracted with a little methylene chloride and the organic phases are combined. The latter are washed in succession with saturated sodium thiosulfate solution, 5% sodium hydroxide solution and water, dried on sodium sulfate and concentrated by evaporation in a vacuum. The purity of the crude product (47.4 g) is sufficient for the further reaction under b). For characterization, 400 mg of the crude product is chromatographed on silica gel with a mixture of ethyl acetate/hexane. 357 mg of 19-(2-bromo-5-methoxyphenyl)-3,3-(2,2-dimethyltrimethylenedioxy)-9α,11α-epoxy-androstane-5α,17β-diol is obtained.

b)

3,3-(2,2-Dimethyltrimethylenedioxy)-11β,19-(4-methoxy-o-phenylene)-androstane-5α,9α,17β-triol 41.4 g (70 mmol) of 19-(2-bromo-5-methoxyphenyl)-3,3-(2,2-dimethyltrimethylenedioxy)-9α,11α-epoxy-androstane-5α,17β-diol, dissolved in 350 ml of absolute diethyl ether, is added under protective gas at room temperature to 435 ml of a 0.8 ethereal methylmagnesium iodide solution. After 30 more minutes of stirring, the reaction mixture is mixed with 825 ml of a 1.6 m n-butyllithium solution (hexane) and stirred overnight. Then, it is carefully poured on ice-cooled, saturated, aqueous ammonium chloride solution, the organic phase is separated and the aqueous phase is extracted with ethyl acetate. The organic phases are combined, washed with saturated, aqueous common salt solution, dried on sodium sulfate and concentrated by evaporation in a vacuum. The crude product (37.2 g) is chromatographed on silica gel with a mixture of ethyl acetate/hexane and 31.3 g of the title compound is obtained as white foam.

Melting point:=254°-255° C. (ethyl acetate)

c)

5α,9α-Dihydroxy-3,3-(2,2-dimethyltrimethylenedioxy)-11β,19-(4-methoxy-o-phenylene)-androstan-17-one 35.1 g of chromium trioxide is added in portions to a mixture of 120 ml of pyridine and 875 ml of methylene chloride at 0° C. Then, 30 g of 3,3-(2,2-dimethyltrimethylenedioxy)-11β,19-(4-methoxy-o-phenylene)-androstane-5α,9α,17β-triol, dissolved in 100 ml of methylene chloride, is instilled slowly at the same temperature and the reaction mixture is stirred for another 1.5 hours at ice bath temperature. After completion of the stirring, the solid components are allowed to settle, the supernatant phase is decanted and the precipitate is washed thoroughly several times with methylene chloride. The combined organic phases are liberated from residual inorganic components by washing with 0.5 m potassium hydroxide solution, washed neutral with water, dried on sodium sulfate and concentrated by evaporation in a vacuum. By chromatography of the residue on silica gel with a mixture of ethyl acetate/hexane, 26.7 g of the title compound is isolated as white foam.

d)

5α,9α-Dihydroxy-3,3-(2,2-dimethyltrimethylenedioxy)-11β,19-(4-hydroxy-o-phenylene)-androstan-17-one 25.5 g (50 mmol) of 5α,9α-dihydroxy-3,3-(2,2-dimethyltrimethylenedioxy)-11β,19-(4-methoxy-o-phenylene)-androstan-17-one is dissolved in 250 ml of absolute dimethylformamide and mixed under protective gas with 14 g of sodium thiomethylate. The reaction mixture is refluxed for 3 hours under inert gas atmosphere, then it is cooled to room temperature and then poured on 4 l of ice water. It is stirred until the crude product is flocculated as white solid. Then; it is suctioned off, washed with a lot of water and dried in a vacuum. 22.6 g of the title compound is obtained as crude product, whose purity is sufficient for the reactions that follow.

e)

5α,9α-Dihydroxy-3,3-(2,2-dimethyltrimethylenedioxy)-11β,19-(4-trifluoromethanesulfonyloxy-o-phenylene)-androstan-17-one 21.85 g (44 mmol) of 5ο,9ο-Dihydroxy-3,3-(2,2-dimethyltrimethylenedioxy)-11β,19-(4-hydroxy-o-phenylene)-androstan-17-one is dissolved in 675 ml of absolute methylene chloride and mixed with 29.8 g of 4-dimethylaminopyridine. The solution is then cooled under protective gas to −70° C. and mixed by slow instillation with 9.7 ml of trifluoromethanesulfonic acid anhydride dissolved in 60 ml of absolute methylene chloride. After 30 more minutes of stirring at −70° C., the reaction mixture is poured on saturated, aqueous sodium bicarbonate solution, the organic phase is separated and the aqueous phase is extracted several times with methylene chloride. The combined organic phases are washed with saturated sodium chloride solution, dried on sodium sulfate and concentrated by evaporation in a vacuum. After chromatography of the residue on silica gel with a mixture of ethyl acetate/hexane, 23.1 g of the title compound is obtained as white foam.

f)

5α,9α-Dihydroxy-3,3-(2,2-dimethyltrimethylenedioxy)-11β,19-4-vinyl-o-phenylene)-androstan-17-one 4 g of 5α,9α-dihydroxy-3,3-(2,2-dimethyltrimethylenedioxy)-11β,19-(4-trifluoromethanesulfonyloxy-o-phenylene)-androstan-17-one is dissolved in 64 ml of absolute dimethylformamide and mixed with 542 mg of lithium chloride, 0.37 g of tetrakistriphenylpalladium and 2.34 ml of tributylvinyltin. Then, the reaction mixture is stirred for 1.5 hours at 110° C. under protective gas and then cooled to room temperature. After filtration on Celite and washing of the filter residue with ethyl acetate, the organic phase is washed with saturated sodium chloride solution, dried on sodium sulfate and concentrated by evaporation in a vacuum. Chromatography of the residue on silica gel with a mixture of ethyl acetate/hexane yields 2.96 g of the title compound as white foam.

g)

5α,9α-Dihydroxy-3,3-(2,2-dimethyltrimethylenedioxy)-11β,19-(4-ethyl-o-phenylene)-androstan-17-one 1.5 g of 5α,9α-dihydroxy-3,3-(2,2-dimethyltrimethylenedioxy)-11β,19-(4-vinyl-o-phenylene)-androstan-17-one is dissolved in 15 ml of absolute tetrahydrofuran and hydrogenated after adding 1.5 ml of pyridine with 150 mg of palladium on barium sulfate (10%) as catalyst at standard pressure. After absorption of one equivalent of hydrogen, the reaction mixture is suctioned off on Celite, the filter residue is rewashed with ethyl acetate and the filtrate is concentrated by evaporation in a vacuum. Crystallization of the crude product from ethyl acetate results in 1.26 g of the title compound.

h)

3,3-2,2-Dimethyltrimethylenedioxy)-11β,19-(4-ethyl-o-phenylene)-17-(prop-1-inyl)-androstane-5α,9α,17β-triol 30 ml of absolute tetrahydrofuran is saturated with propine at 0° C. Then, 3.7 ml of a 1.6 m butyllithium solution (hexane) is slowly instilled in this solution without a sizeable temperature increase. After 15 more minutes of stirring, a solution of 300 mg of 5α,9α-dihydroxy-3,3-(2,2-dimethyltrimethylenedioxy)-11β,19-(4-ethyl-o-phenylene)-androstan-17-one, dissolved in 6 ml of absolute tetrahydrofuran, is instilled slowly, with ice bath cooling, in this reaction mixture and allowed to stir overnight. Then, the reaction mixture is poured on water, the aqueous phase is extracted with ethyl acetate and the organic phase is washed with sodium chloride solution. After drying on sodium sulfate and concentration by evaporation of the organic phase in a vacuum, the residue is chromatographed on aluminum oxide (neutral, stage III). 295 mg of the title compound is obtained as white foam.

i)

9α,17β-Dihydroxy-11β,19-(4-ethyl-o-phenylene)-17-(prop-1-inyl)-4-androsten-3-one 280 mg of 3,3-(2,2-dimethyltrimethylenedioxy)-11β,19-(4-ethyl-o-phenylene)-17-(prop-1-inyl)-androstane-5α,9α,17β-triol is dissolved in 20 ml of acetone and mixed with 0.1 ml of 4 n aqueous hydrochloric acid. After 3 more hours of stirring at 40° C., the reaction mixture is poured on saturated sodium bicarbonate solution and the aqueous phase is extracted with methylene chloride. The combined organic phases are washed with saturated sodium chloride solution, dried on sodium sulfate and concentrated by evaporation in a vacuum. After chromatography of the residue on silica gel with a mixture of ethyl acetate/hexane, 234 mg of the title compound is obtained as white foam.

Melting point:=155°-160° C. (hexane/methylene chloride)

EXAMPLE 2

9α,17β-Dihydroxy-11β,19-(4-vinyl-o-phenylene)-17-(prop-1-inyl)-4-androsten-3=one a)

3,3-(2,2-Dimethyltrimethylenedioxy)-11β,19-(4-vinyl-o-phenylene)-17-(prop-1-inyl)-androstane-5α,9α,17β-triol Analogously to the instructions described under example 1h), 1 g of the keto compound produced under f is converted to the corresponding 17-propinyl compound. 0.97 g of the above-named compound is obtained as white foam.

b)

9α,17β-Dihydroxy-11β,19-(4-vinyl-o-phenylene)-17-(prop-1-inyl)-4-androsten-3-one Analogously to the instructions described under example 1i) 0.9 g of the propinyl compound produced under d) is reacted. 660 mg of the title compound is obtained as white foam.

Melting point:=171°-175°-C. (diisopropyl ether/methylene chloride)

EXAMPLE 3

9α,17β-Dihydroxy-11β,19-[4-(3-pyridyl)-o-phenylene]17-(prop-1-inyl)-4-androsten-3-one a)

5α,9α-Dihydroxy-3,3-(2,2-dimethyltrimethylenedioxy)-11β,19-(4-tri-n-butylstannyl-o-phenylene)-androstan-17-one 2.6 g of the triflate produced under example 1e) is dissolved in 41 ml of absolute dioxane and mixed under protective gas with 6.2 ml of hexa-n-butyltin, 521 mg of lithium chloride and 190 mg of tetrakistriphenylphosphine palladium. Then, the reaction mixture is heated to 110° C., stirred for 1 more hour, cooled to room temperature and concentrated by evaporation in a vacuum. The residue is chromatographed on silica gel with a mixture of ethyl acetate/hexane. 2.75 g of the above-named compound is obtained as white foam.

b)

5α,9α-Dihydroxy-3,3-(2,2-dimethyltrimethylenedioxy)-11β,19-[4-(3-pyridyl)-o-phenylene]-androstan-17-one 2.7 g of the tinorganyl produced under a) is dissolved in 41 ml of absolute toluene, mixed with 190 mg of tetrakistriphenylphosphine palladium and 4 ml of 3-bromopyridine. Then, the reaction mixture is heated for 17 hours to 110° C., cooled to room temperature and concentrated by evaporation in a vacuum. The residue is chromatographed on silica gel with a mixture of ethyl acetate/hexane. 1.47 g of the above-named compound is obtained as white foam.

c)

3,3-(2,2-Dimethyltrimethylenedioxy)-11β,19-[4-(3-pyridyl-o-phenylene]-17-(prop-1-inyl)-androstane-5α,9α,17β-triol Analogously to the instructions described under example 1h),˙400 mg of the keto compound produced under b) is converted to the corresponding 17-propinyl compound. 402 mg of the above-named compound is obtained as white foam.

9α,17β-Dihydroxy-11β,19-[4-(3-pyridyl)-o-phenylene]-17-(prop-1-inyl)-4-androsten-3-one Analogously to the instructions described under example 1i), 380 mg of the propinyl compound produced under c) is reacted. 288 mg of the title compound is obtained as white foam.

Melting point:=203°-205° C. (diisopropyl ether)

EXAMPLE 4

9α,17β-Dihydroxy-11β,19-(4-mathoxy-o-phenylene)-4-androsten-3-one

Analogously to the instruction described under example 1i), 0.5 g of the hydroxy compound produced under example 1b) is reacted. 306 mg of the title compound is obtained as white foam.

Melting point:=175°-177° C. (ethyl acetate)

EXAMPLE 5

9α,17β-Dihydroxy-11β,19-(4-hydroxy-o-phenylene)-4-androsten-3-one a)

3,3-(2,2-Dimethyltrimethylenedioxy)-11β,19-(4-hydroxy-o-phenylene)-androstane-5α,9α17β-triol Analogously to the instructions described under example 1d), 2.5 g of the methoxy compound produced under example 1b) is reacted. After chromatography on silica gel with a mixture of ethyl acetate/hexane, 2.15 g of phenol is obtained as white foam.

b)

9α,17β-Dihydroxy-11β,19-(4-hydroxy-o-phenylene)-4-androsten-3-one

Analogously to the instructions described under example 1i), 750 mg of the phenol produced under a) is reacted. 394 mg of the title compound is obtained as white foam.

Melting point: =146°-148° C. (ethyl acetate)

EXAMPLE 6

9α,17β-Dihydroxy-11β,19-[4-(4-cyanophenyl)-o-phenylene]-4-androsten-3-one a)

3,3-(2,2-Dimethyltrimethylenedioxy)-11β,19-(4-trifluoromethanesulfonyloxy-o-phenylene)-androstane-5α,9α17β-triol Analogously to the instructions described under example 1e), 1.25 g of the phenol produced under example 5a) is reacted. After chromatography on silica gel with a mixture of ethyl acetate/hexane, 1.3 g of triflate is obtained as white foam.

b)

3,3-(2,2-Dimethyltrimethylenedioxy)-11β,19-(4-tri-n-butylstannyl-o-phenylene)-androstane-5α,9α,17β-triol Analogously to the instructions described under example 3a), 1.25 g of the triflate produced under a) is reacted. After chromatography on silica gel with a mixture of ethyl acetate/hexane, 1.53 g of tinorganyl is obtained as white foam.

c)

3,3-(2,2-Dimethyltrimethylenedioxy)-11β,19-[4-(4-cyanophenyl)-o-phenylene]-androstane-5α,9α,17β-triol Analogously to the instructions described under example 3b), 1.5 g of the tinorganyl produced under b) is reacted with 4 g of 4-bromobenzonitrile. After chromatography on silica gel with a mixture of ethyl acetate/hexane, 0.73 g of coupling product is obtained as white foam.

d)

9α,17β-Dihydroxy-11β,19-[4-(4-cyanophenyl)-o-phenylene]-4-androsten-3-one

Analogously to the instructions described under example 1i), 700 mg of the benzonitrile produced under c) is reacted. 512 mg of the title compound is obtained as white foam.

Melting point: =186°-190° C. (diisopropyl ether)

EXAMPLE 7

11β,19-(4-Dimethylamino-o-phenylene)-9α,17β-dihydroxy-17-(prop-1-inyl)-4-androsten-3-one a)

19-(3-Dimethylaminophenyl)-3,3-(2,2-dimethyltrimethylenedioxy)-9(11)-androstene-5α,17β-diol 10 g of 19-(2-chloro-5-dimethylaminophenyl)-3,3-(2,2-dimethyltrimethylenedioxy)-9(11)-androstene-5α,17β-diol is introduced in 500 ml of methanol under protective gas and mixed in succession with 5.8 g of ammonium formate and 2.5 g of palladium on carbon (10%). After 18 more hours of stirring at room temperature, the reaction mixture is filtered on Celite, the filtrate is concentrated by evaporation in a vacuum and the residue is taken up in methylene chloride. The organic phase is washed with water, dried on sodium sulfate and concentrated by evaporation in a vacuum. The purity of the crude product is sufficient for further reactions. 100 mg of the substance is chromatographed on silica gel with a mixture of hexane/ethyl acetate for complete characterization. 73 mg of the above-named compound is isolated as white foam.

b)

19-(2-Bromo-5-dimethylaminophenyl)-3,3-(2,2-dimethyltrimethylenedioxy)-9(11)-androstene-5α,17β-diol 9 g of the crude product produced under a) is introduced at 0° C. in 450 ml of methylene chloride and mixed in succession with 3.1 ml of triethylamine and 3.78 g of N-bromosuccinimide. After 45 more minutes of stirring at ice bath temperature, saturated sodium thiosulfate solution is added and the aqueous phase is extracted with methylene chloride. The combined organic phases are washed with water, dried on sodium sulfate and concentrated by evaporation in a vacuum. The residue is chromatographed on silica gel with a mixture of hexane/ethyl acetate. 9.7 g of the above-named compound is obtained as white foam.

c)

N-<4-Bromo-3-[9α,11α-epoxy-5α,17β-dihydroxy-3,3-(2,2-dimethyltrimethylenedioxy)-androstan-19-yl]-phenyl>-N,N-dimethylaminoxide 100 ml of a 0.5 m sodium bicarbonate solution and 18.2 g of m-chloroperbenzoic acid (67.7%) are added in succession to a solution of 8.2 g of the bromide, produced under b), in 160 ml of absolute methylene chloride. Then, the reaction mixture is stirred for 1 more hour at room temperature, then mixed with 5% sodium hydroxide solution, the organic phase is separated and the aqueous phase is extracted with methylene chloride. The combined organic phases are dried on sodium sulfate and concentrated by evaporation in a vacuum. The obtained crude product (9.1 g) is used directly in the following reaction.

d)
11β,19-(4-Dimethylamino-o-phenylene)-3,3-(2,2-dimethyltrimethylenedioxy)-androstane-5α,9α,17β-triol Analogously to the instructions described under example 1c), 9.1 g of the crude product obtained under c) is reacted with 140 ml of a 1 m ethereal methylmagnesium iodide solution and 360 ml of a 1.6 m n-butyllithium solution (hexane). After chromatography on silica gel with a mixture of hexane/ethyl acetate, 3.54 g of the above-named compound is isolated as white foam.

$^1$H-NMR (CD$_2$C1$_2$) [δ]ppm: 7.18 (1H,d,J=9,5Hz); 6.59 (1H,dd,J=9.5 and J$_1$=2Hz); 6.39 (1H,d,J$_1$=2Hz); 5.87 (1H,s); 5.36 (1H,s); 3 68 (1H,m); 3.65-3.35 (4H,m); 3.15 (1H,d,J$_2$=17.5 Hz); 2.94 (1H,m); 2.87 (6H,s); 2.75 (1H,d,J$_2$=17.5Hz); 1.02 (3H,s); 0.96 (3H,s); 0.22 (3H,s).

e) 11β,19-(4-Dimethylamino o-phenylene)-3,3-(2,2-dimethyltrimethylenedioxy)-5α,-9α-dihydroxy-androstan-17-one 700 mg of N-chlorosuccinimide is introduced at 0° C. in 70 ml of absolute methylene chloride. After instillation of 0.49 ml of dimethyl sulfide, the mixture is stirred for 30 more minutes. Then, 3.5 g of the 17-hydroxy compound, produced under d), dissolved in 35 ml of absolute methylene chloride is slowly instilled. After 1.5 more hours of stirring under exclusion of moisture, 0.91 ml of triethylamine is added to the reaction mixture. Then, it is poured on water, the aqueous phase is extracted with methylene chloride and the organic phase is washed with saturated sodium chloride solution. Then, it is dried on sodium sulfate and concentrated by evaporation in a vacuum. After chromatography of the residue on silica gel with a mixture of hexane/ethyl acetate, 2.98 g of the above-named ketone is obtained as white foam.

f)
11β,19-(4-Dimethylamino-o-phenylene)-3,3-(2,2-dimethyltrimethylenedioxy)-17-(prop-1-inyl)-androstane-5α,9α,17β-triol Analogously to the instructions described under example 1h), 0.5 g of the keto compound, produced under e), is converted to the corresponding 17-propinyl compound. 473 mg of the above-named compound is isolated as white foam.

g)
11β,19-(4-Dimethylamino-o-phenylene)-9α,17β-dihydroxy-17-(prop-1-inyl)-4-androstan-3-one Analogously to the instructions described under example 1i), 450 mg of the 17-propinyl compound produced under g) is converted to the title compound. 212 mg of the above-named compound is isolated as white foam.

$^1$H-NMR (CDCl$_3$) [δ] ppm: 7.23 (1H,d,J=9,5Hz); 6.63 (1H,dd,J=9.5 and J$_1$=2Hz); 6.42 (1H,d,J$_1$=2Hz); 5.99 (1H,s); 3.4 (1H,d,J$_2$=17.5Hz); 3.13 (1H,m); 2.93 (6H,s); 2.86 (1H,d,J$_2$=17.5Hz); 1.9 (3H,s); 0.4 (3H,s).

EXAMPLE 8

11β,19-(4-Ethyl-o-phenylene)-5α,9α-dihydroxyandrostane-3,17-dione 500 mg of the keto compound produced under example 1g) is reacted in 10 ml of 70% acetic acid at 0° C. to the title compound (about 60 minutes of stirring). The resulting reaction mixture is diluted with water and the aqueous phase is extracted with methylene chloride. The combined organic phases are washed in succession with saturated sodium bicarbonate solution and saturated common salt solution and then dried on sodium sulfate. After concentration by evaporation in a vacuum, the residue is chromatographed on silica gel. 212 mg of the title compound is isolated as white foam.

Melting point:=155°-160° C. (ethyl acetate)

EXAMPLE 9

9α,17β-Dihydroxy-17-methyl-11β,19-[4-(3-pyridyl)-o-phenylene]-4-androsten-3-one a)
3,3-(2,2-Dimethyltrimethylenedioxy)-17-methyl-11β,19-[4-(3-pyridyl)-o-phenylene]-androstane-5α,-9α,17β-triol 1.1 g of 5α,9α-dihydroxy-3,3-(2,2-dimethyltrimethylenedioxy)-11β,19-[4-(3-pyridyl)-o-phenylene]-androstan-17-one dissolved in 15 ml of absolute tetrahydrofuran is instilled slowly at 0° C. in 17.2 ml of a 1 6 m solution of methyllithium in diethyl ether. Then, the reaction mixture is poured on ice-cooled, saturated ammonium chloride solution and the aqueous phase is extracted with ethyl acetate. After drying the combined organic phases on sodium sulfate and concentration by evaporation in a vacuum, the residue is chromatographed on silica gel with a mixture of methanol/ethyl acetate. 135 mg of the initial material is recovered and 875 mg of the above-named compound is obtained as white foam.

9α,17β-Dihydroxy-17-methyl-11β,19-[4-(3-pyridyl)-o-phenylene]-4-4-androsten-3-one Analogously to the instructions described under example 1i), 800 mg of the methyl compound produced under a) is reacted. 535 mg of the title compound is obtained as white foam.

$^1$H-NMR (CDCl$_3$) [δ] ppm: 8.57 (1H,dd,J$_1$=5Hz and J$_2$=0.5Hz); 7.88 (1H,d broad,J=8,5Hz); 7.28-7.55 (5H,m); 6.02 (1H,s); 3.54 (1H,d,J=17.5Hz); 3.23 (1H,d broad, J=5Hz); 2.99 (1H,d,J=17.5Hz); 1.3 (3H,s); 0.4 (3H,s).

[α]$^{20}$D=+46° (CHCl$_3$; c=0.505)

EXAMPLE 10

9α,17β-Dihydroxy-17-(3-hydroxyprop-1-inyl)-11β,19-]4-(3-pyridyl)-o-phenylene]-4-androsten-3-one a)
3,3-(2,2-Dimethyltrimethylenedioxy)-17-(3-hydroxyprop-1-inyl)-11β,19-[4-(3-pyridyl) o phenylene]-androstane-5α,9α,17β-triol 5.5 ml of propargyl alcohol and 3.8 g of 5α,9α-dihydroxy-3,3-(2,2-dimethyltrimethylenedioxy)-11β,19-[4-(3-pyridyl)-o-phenylene]-androstan-17-one are introduced in 100 ml of absolute tetrahydrofuran under protective gas at 0° C., then mixed with 15.7 g of potassium ethylate and the reaction mixture is stirred overnight with slow heating to room temperature. Then, it is poured on ice-cooled, saturated ammonium chloride solution and the aqueous phase is extracted with ethyl acetate. After drying of the combined organic phases on sodium sulfate and concentration by evaporation in a vacuum, the residue is chromatographed on silica gel with a mixture of methanol/ethyl acetate. 260 m of the initial material is recovered and 4.09 g of the above-named compound is obtained as white foam.

b)

9α,17β-Dihydroxy-17-(3-hydroxyprop-1-inyl)-11β,19-[4-(3-pyridyl)-o-phenylene]-4-androsten-3-one Analogously to the instructions described under example 1i), 4 g of the hydroxypropinyl compound produced under a) is reacted. 2.48 g of the crystalline title compound is obtained from ethyl acetate.

Melting point: 206°–208° C. (ethyl acetate)
$[\alpha]^{20}D = +=°$ (CHCl$_3$; c=0.505)

EXAMPLE 11

9α,17β-Dihydroxy-17-(3-hydroxyprop-1-(Z)-enyl)-11β,19-[4-(3-pyridyl)-o-phenylene]-4-androsten-3-one 1.7 g of 9α,17β-dihydroxy-17-(3-hydroxyprop-1-inyl)-11β,19-[4-(3-pyridyl)-o-phenylene]-4-androsten-3-one is dissolved in a mixture of 17 ml of tetrahydrofuran and 17 ml of ethanol, mixed with 1.7 ml of pyridine and hydrogenated as catalyst at standard pressure by using 170 mg of palladium (10%) on barium sulfate. After absorption of one equivalent of hydrogen, the reaction mixture is filtered on Celite, the filter residue is rewashed with ethyl acetate and the filtrate is concentrated by evaporation in a vacuum. The residue is recrystallized from ethanol. 1.3 g of the title compound is obtained.

Melting point: 255°–257° C. (ethanol)
$[\alpha]^{20}D = +92°$(CHCl$_3$; c =0.505)

EXAMPLE 12

2′,5′-Dihydro-11β,19-[4-(3-pyridyl)-o-phenylene]-9α-hydroxy-spiro-[androst-4ene-17β,2′-furan1-3-one At 0° C., 1.5 g of 9α,17β-dihydroxy-17-(3-hydroxyprop-1-(2)-enyl)-11β19-[4-(3-pyridyl)-o-phenylene]-4-androsten-3-one is introduced in 50 ml of absolute dimethylformamide and mixed with 4.3 ml of triethylamine. After adding 0.6 ml of methanesulfonic acid chloride, the reaction mixture is stirred for 2 more hours at 0° C. Then, it is poured on saturated sodium bicarbonate solution and the aqueous phase is extracted with methylene chloride. The combined organic phase are washed with saturated sodium chloride solution, dried on sodium sulfate and concentrated by evaporation in a vacuum. The residue is chromatographed on silica gel with a mixture of ethyl acetate/hexane and 1.15 g of the title compound is obtained.

$^1$H-NMR (CDCl$_3$) [δ] ppm: 8.85 (1H,s broad); 8.58 (1H, m); 7.88 (1H,m); 7.3–7.55 (5H,m); 6.03 (1H, s); 5.87–5.97 (2H,m); 4.55–4.7 (2H,m); 3.54 (1H,d,J=17.5HZ); 0.45 (3H,s).

EXAMPLE 13

9α,17β-Dihydroxy-17-(ethinyl)-11β,19-[4-(3-pyridyl)-o-phenylene]-4-androsten-3-one a)

3,3-(2,2-Dimethyltrimethylenedioxy)-17-ethinyl)-11β,19-[4-(3-pyridyl)-o-phenylene]-androstane-5α,-9α,17β-triol Analogously to the instructions described under example 1h), 2 g of the ketone produced under example 3c) is reacted to the ethinyl compound. 1.98 g of the above-named compound is obtained as white foam.

b)

9α,17β-Dihydroxy-17-(ethinyl)-11β,19-[4-(3-pyridyl)-o-phenylnel]-4-androsten-3-one Analogously to the instructions described under example 1i), 1.9 g of the ethinyl compound produced under a) is reacted. 1.28 g of the crystalline title compound is obtained from ethyl acetate.

Melting point: 240°–242° C. (ethyl acetate)
$[\alpha]^{20} D = +92+$(CHCl$_3$; c=0.505)

We claim:

1. 9α-Hydroxy-19,11β-bridged steroids of formula I

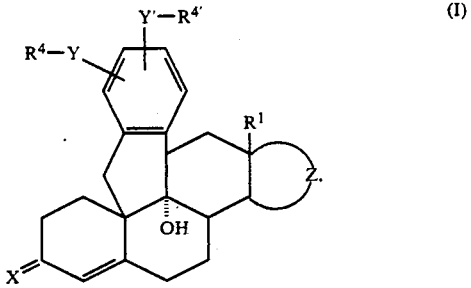

in which
R$^1$ stand for a methyl or ethyl radical,
X stands for an oxygen atom, two hydrogen atoms or a hydroxyimino grouping, NOH,
Z stands for the radical of the ring formula

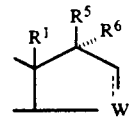

in which
R$^1$ has the meaning mentioned in formula I, the dotted line starting from W means optional presence of a double bond,
W means a CH$_2$, CH, CH$_2$CH$_2$ or CHCH$_2$ radical,
R$^5$/R$^6$ means —OR$^7$/—C≡C—U

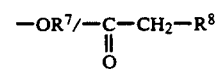

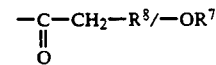

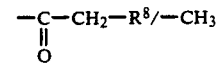

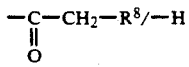

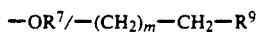

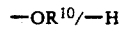

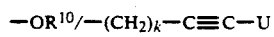

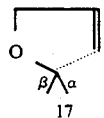

17

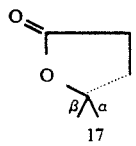

17

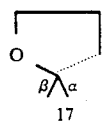

17 with $R^7$ meaning a hydrogen atom or alkane carboxylic acid acyl radical with 1 to 4 carbon atoms, U meaning a hydrogen atom, an alkyl, hydroxyalkyl, alkoxyalkyl, alkanoyalkyl group each with 1 to 4 carbon atoms in the alkyl radical(s) or a halogen atom, $R^8$ meaning a hydrogen atom, a hydroxy group, an alkyl, o-alkyl or alkanoyl group each with 1 to 4 carbon atoms, $R^9$ meaning a hydrogen atom, a hydroxy or cyanide radical, and O-alkyl or alkanoyl group each with 1 to 4 carbon atoms, $R^{10}$ meaning a hydrogen atom, an alkyl or, together with oxygen, an alkanoyl or benzoyl group, each with 1 to 10 carbon atoms, m meaning 0, 1, 2 or 3, k meaning 0, 1 or 2, in which $R^4$ and $R^{4'}$, which are the same or different, each stands for a hydrogen atom, a cyanide radical, an $-OR^{11}$, $-S(O)_kR^{11}$, $-N(O)_nR^{11}R^{12}$, $-O-SO_2R^{13}$, $-P(O)(OR^{14})_2$, $-SiR^{14}_3$ or $-SnR^{14}_3$ group with k meaning numbers 0, 1 or 2, n meaning numbers 0 or 1, $R^{11}$ meaning a hydrogen atom or a $C_1-C_8$ alkyl radical, provided that k and n are greater than 0 only if $R^{11}$ is $C_1-C_8$ alkyl, $R^{12}$ meaning $R^{11}$, a cyanide or a $C_1-C_{10}$ alkyl or benzyl carboxylic acid acyl radical, $R^{13}$ meaning a perfluorinated $C_1-C_4$ alkyl radical, $R^{14}$ meaning a $C_1-C_4$ alkyl radical or $R^{11}$ and $R^{12}$ form a 5- or 6-membered heterocyclic ring inside an $-N(O)_nR^{11}R^{12}$ group together with the inclusion of N, and still another heteroatom N, O or S can be contained in the ring in a position non-adjacent to the nitrogen, Y and Y', which are the same or different, each means a direct bond, a straight-chain or branched, alkylene group with up to 20 carbon atoms optionally exhibiting one or more double or triple bonds, the alkylene group is optionally substituted by one or more oxo, $C_1-C_{10}$ alkanoyl or benzoyl, $-OR^{11}$, $-S(O)_kR^{11}$ and/or $-N(O)_nR^{11}R^{12}$ groups, an optionally substituted phenylene radical, or $R^4$—Y and $R^{4'}$—Y' independently or together mean the radical of a saturated, unsaturated or aromatic 5- or 6-membered ring optionally substituted with 0 to 2 oxygen atoms, sulfur atoms and/or $N^{11}$ groups in the ring in non-adjacent positions, as well as their pharmaceutically compatible addition salts with acids.

2. Compounds according to claim 1, wherein Y and Y', each stand for a direct bond and $R^4$ and $R^{4'}$ each stands for a hydrogen atom.

3. Compounds according to claim 1, wherein Y and Y' each stand for a direct bond, $R^4$ stand for a hydrogen atom and $R^{4'}$ stands for a nitrogen atom, substituted with two $C_1-C_8$ alkyl radicals.

4. Compounds according to claim 1, wherein Y and Y' each stands for a direct bond, $R^4$ stands for a hydrogen atom and $R^{4'}$ stands for a $C_1-C_8$ alkoxy group.

5. Compounds according to claim 1, wherein Y stands for a direct bond, $R^4$ and $R^{4'}$ each stands for a hydrogen atom and Y' stands for a straight-chain or branched alkylene group with up to 20 carbon atoms optionally exhibiting one or more a double and/or triple bonds, the alkylene group is substituted by an oxo or $OR^{11}$ group.

6. Compounds according to claim 1, wherein $R^4$—Y and $R^{4'}$—Y' together stand for the radical of a saturated, unsaturated or aromatic 5- or 6-membered ring substituted with 0 to 2 oxygen atoms, sulfur atoms and/or $NR^{11}$ groups in the ring in non-adjacent positions.

7. Compounds according to claim 1, wherein Y'—$R^{4'}$ is a hydrogen atom and Y-$R^4$ is an ethyl, vinyl, isopropyl, isopropenyl, prop-1(Z)-enyl, prop-1(E)-enyl, prop-2-enyl, ethinyl, propinyl, prop-2-inyl, methoxy, thiomethyl, thioethyl, 1-hydroxyethyl or diethoxyphosphoryl group; or an optionally substituted radical of a saturated, unsaturated, or aromatic ring optionally substituted with 0 to 2 oxygen atoms, sulfur atoms and/or $NR^{11}$ groups in the ring in non-adjacent positions.

8. Compounds according to claim 7, wherein the radical of a saturated, unsaturated or aromatic ring is a phenyl, naphthyl, 2-methoxyphenyl, 3-methoxyphenyl, 4-methoxyphenyl, 2-tolyl, 3-tolyl, 4-tolyl, 2-dimethylaminophenyl, 3-dimethylaminophenyl, 4-dimethylaminophenyl, furyl-2, furyl-3, thienyl-2, thienyl-3, pyridyl-2, pyridyl-3, pyridyl-4, pyrimidinyl, thiazolyl, or imidazolyl radical.

9. A process for preparing the compounds of claim 1, wherein a compound of formula III

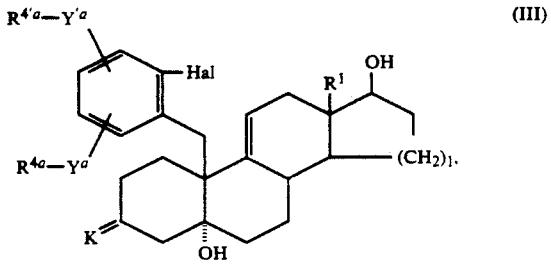

(III)

in which $R^1$ means a methyl or ethyl radial, l meaning the number 1 or 2,

K means a keto group blocked in the form of the ketal or thioketal, and

Hal means a chlorine, bromine or iodine atoms, $R^{4a}$, $R^{4'a}$, $Y^1$ and $Y'^a$, with exclusion of the cyanide radical, have the same meaning as $R^4$, $R^{4'}$, Y and Y', and optionally present hydroxy, mercapto, amino, oxo and/or terminal acetylene groups are protected by an alkoxy, alkoxyalkyl, tetrahydropyran, ketal, thioketal or silyl group, is epoxidated to a compound of the formula II

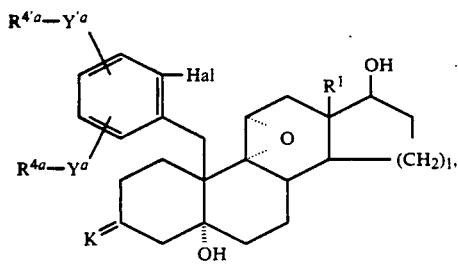

in which $R^1$, l, K, Hal and $R^{4a}$, $Y^1$, $R^{4'a}$, $Y'^1$ have the same meaning as in formula I, epoxidated compound II then is cyclized to an intermediate product of the formula IVa

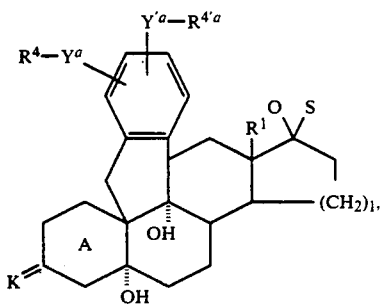

in which $R^{4a}$, $R^{4'a}$, $Y^a$ and $Y'^a$, with exclusion of the cyanide radical, have the same meaning as $R^4$, $R^{4'}$, y and Y', and optionally present hydroxy, mercapto, amino, oxo and/or terminal acetylene groups are protected by the same groups indicated above, and Q exclusively means a β-hydroxy group and S exclusively means an α-hydrogen atom, and then first either a) the c-17 hydroxy group optionally is oxidized an then b) optionally a hydroxy group, exhibiting one of the stated protecting groups is liberated from this protecting group in the 19,11β-phenylene ring, a corresponding perfluoroalkylsulfonate optionally is produced form the hydroxy compound, the perfluoroalkylsulfonate is converted to a compound optionally either directly or by exchange of the perfluoroalkylsulfonate leaving group for a tin trialkyl group by the corresponding tin trialkyl compound, which exhibits the desired substitution pattern in the 19,11β-phenylene ring, or first b) and then a) are performed and then c) ring D is functionalized with the substituents $R^5/R^6$ defined in claim 1, the thus obtained product from the action of adehydratign agent, which is also capable of releasing the 3-oxo group, is subjected to dehydration with the simultaneous formation of the 4(5)-double bond, and optionally the release of the 3-oxo group and the dehydration taking place in succession, and then, optionally after renewed protection of intermediately released functional groups contained in the 19,11β-phenylene ring and/or Z, the desired functions of rings A and B of the steroid skeleton is introduced or d) the thus obtained product of the action of a dehydrating agent, which is also capable of releasing the 3-oxo group, is subjected to the dehydration with the simultaneous formation of the 4(5)-double bond, the desired functions of rings A and B of the steroid skeleton are introduced and then, after protection of the 3-oxo group, ring D is functionalized as stated above, or steps 2) and b) are performed after step c) or d), the thus obtained product optionally is liberated from protecting groups, the hydroxy, mercapto and/or amino group or groups optionally contained in the 19,11β-phenylene ring optionally is introduced in the aryl substituent or substituents, the amino and/or sulfide group or groups optionally contained int eh aryl substituent or substituents optionally are oxidized, optionally are reacted with hydroxylamine-hydrochloride to the product of formula I with X meaning the hydroxyimino grouping NOH as well as a pharmaceutically compatible acid addition salt optionally is produced.

10. A pharmaceutical preparation as an antigestagen, antiglucocorticoidal or antimineralcorticoidal agent comprising a compound of claim 1 and a pharmaceutically acceptable carrier.

* * * * *